(12) United States Patent
Takae et al.

(10) Patent No.: US 8,532,260 B2
(45) Date of Patent: Sep. 10, 2013

(54) MOBILE X-RAY APPARATUS

(75) Inventors: Tomokazu Takae, Tokyo (JP); Miyuki Fuse, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 317 days.

(21) Appl. No.: 13/003,097

(22) PCT Filed: Jun. 22, 2009

(86) PCT No.: PCT/JP2009/061274
§ 371 (c)(1),
(2), (4) Date: Jan. 7, 2011

(87) PCT Pub. No.: WO2010/004855
PCT Pub. Date: Jan. 14, 2010

(65) Prior Publication Data
US 2011/0110498 A1    May 12, 2011

(30) Foreign Application Priority Data
Jul. 10, 2008    (JP) ................................. 2008-180307

(51) Int. Cl.
*H05G 1/10*    (2006.01)
(52) U.S. Cl.
USPC ........................... 378/102; 378/98.5; 378/198

(58) Field of Classification Search
USPC ................... 378/91, 98, 98.2, 98.5, 101, 102, 378/198
See application file for complete search history.

(56) References Cited

U.S. PATENT DOCUMENTS

| 6,437,699 B1 | 8/2002 | Hayakawa |
| 2006/0120512 A1 | 6/2006 | Watanabe |

FOREIGN PATENT DOCUMENTS

| JP | 3078286 | 8/2000 |
| JP | 2001-147259 | 5/2001 |
| JP | 2005-006888 | 1/2005 |
| JP | 2005304696 | 11/2005 |
| JP | 2006095020 | 4/2006 |
| JP | 2006-158508 | 6/2006 |

*Primary Examiner* — Jurie Yun
(74) *Attorney, Agent, or Firm* — Brundidge & Stanger, P.C.

(57) ABSTRACT

A technique for aiding the determination of whether or not desired imaging can be performed by a mobile-type X-ray apparatus for X-ray imaging using a battery mounted therein as a drive source. From the imaging list showing scheduled imaging and pre-stored information about the power consumed when each region is imaged, a prediction of the consumption of the battery power of when all the imaging in the imaging list is performed is computed and presented together with the remaining battery power to the user. Various corrections can be applied to the computation. The difference between the remaining battery power and the predicted consumption of the battery power may be displayed.

12 Claims, 9 Drawing Sheets

MOBILE X-RAY APPARATUS

FIELD OF THE INVENTION

The present invention relates to an operation management technique of a mobile-type X-ray apparatus for executing X-ray imaging by making the rounds in hospitals, particularly to a technique for monitoring power consumption amount of batteries provided to a mobile-type X-ray apparatus.

DESCRIPTION OF RELATED ART

Battery-driven devices are generally provided with the function to detect and display available power supply at the present point (remaining battery power) (for example, refer to Patent Document 1). Mobile-type X-ray apparatuses that are movable for making the rounds in hospitals to execute X-ray imaging also use batteries as a drive source for X-ray irradiation. Thus they also have a function which displays remaining battery power to indicate the timing for exchanging batteries and the remaining time for operating the device.

PRIOR ARTS

Patent Document 1: Japanese Patent No. 3078286

However, since power consumption of a battery is different in each imaging condition, it is difficult to predict whether or not the remaining power of battery is able to complete the entire scheduled imaging by referring only to the remaining battery power. Particularly a mobile-type X-ray apparatus often uses a battery not only as the drive source for X-ray imaging but also as the power source for moving, which makes it more difficult to predict the timing for recharging the battery. This problem sometimes causes the condition that the battery is expended after moving the X-ray apparatus. In order to avoid such situations, an extra amount of battery power needs to be consistently charged up which often incurs waste.

The object of the present invention is to provide a technique to support determining if the remaining amount of battery power is enough to execute desired quantity of imaging by using a mobile-type X-ray apparatus driven by a mounted battery, considering the above-mentioned problem.

BRIEF SUMMARY OF THE INVENTION

The present invention, based on the imaging list of the scheduled imaging and the pre-stored power consumption information for each target region, calculates the predictive amount of battery power consumption for completing the entire imaging on the imaging list and displays the calculated amount along with the remaining battery power to an operator.

In concrete terms, it provides the mobile-type X-ray apparatus provided with a battery for executing X-ray imaging, comprising:

remaining battery power detecting means configured to detect remaining power of a battery;

predictive power consumption calculating means configured to calculate predictive battery power consumption based on an imaging list for making the rounds; and display means configured to display the remaining power and the predictive battery power consumption.

In accordance with the present invention, it is possible to easily determine if the entire planned imaging can be executed by a mobile-type X-ray apparatus using a battery as its drive source.

BRIEF DESCRIPTION OF THE DIAGRAMS

DETAILED DESCRIPTION OF THE INVENTION

An embodiment related to the present invention will be described below referring to the attached diagrams. In all the diagrams, the same function parts are represented by the same reference numerals, and the duplicative description thereof is omitted.

Figure 1:
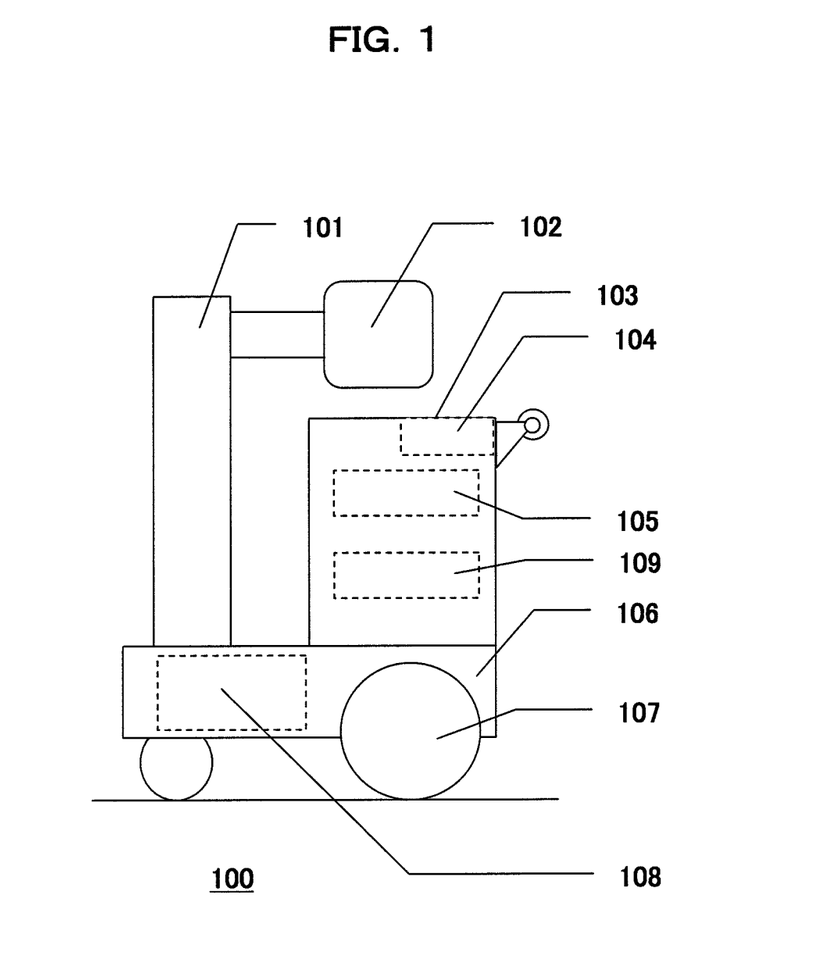
FIG. 1 is a block diagram of a substantial part in the mobile-type X-ray apparatus related to an embodiment of the present embodiment.

FIG. 1 is a block diagram of a substantial part of mobile-type X-ray apparatus 100 in the present embodiment. Mobile-type X-ray apparatus 100 of the present embodiment comprises motor- or manually-driven mobile carriage 106, wheels 107, rechargeable battery 108, X-ray generator 102 for irradiating X-rays, main body 101 for supporting the X-ray generator via an arm, imaging controller 109 for controlling imaging, input unit 103, display unit 104 and power consumption controller 105, as shown in the diagram.

Figure 2:
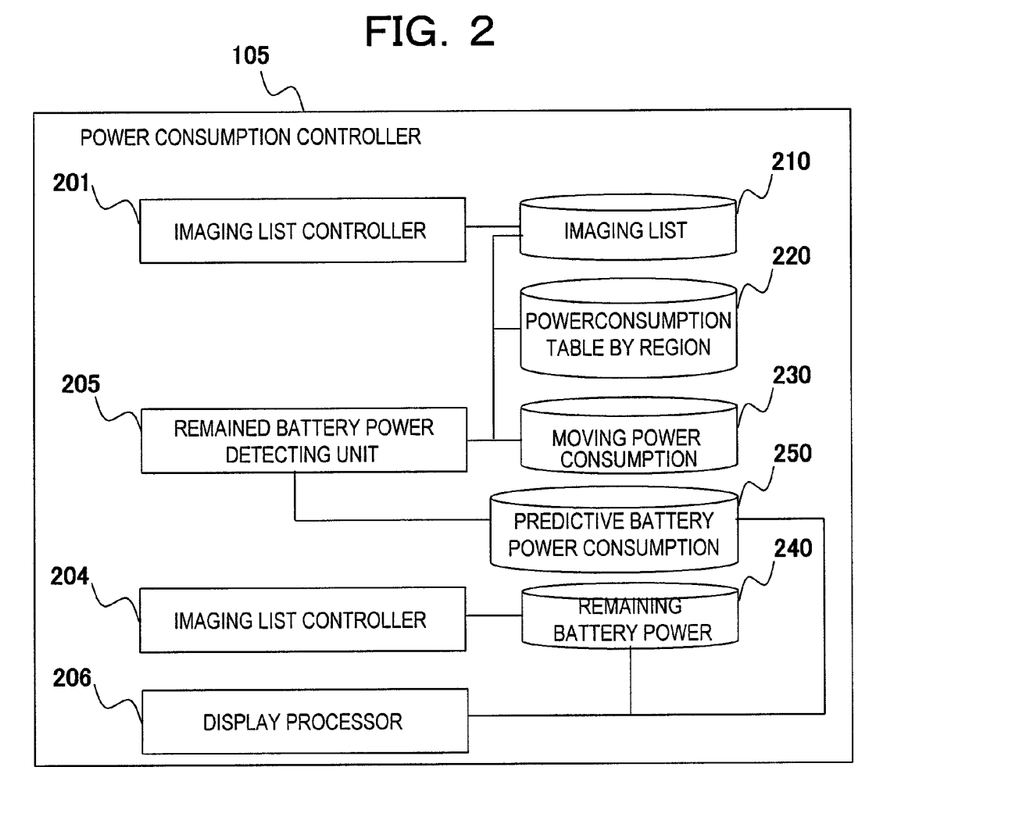
FIG. 2 is a functional block diagram of a power consumption controller in an embodiment of the present embodiment.

In the present embodiment, the predictive power consumption of rechargeable battery 108 is calculated in power consumption controller 105. FIG. 2 is a functional block diagram of power consumption controller 105 of the present embodiment. Power consumption controller 105 comprises imaging list controller 201, remaining battery power detecting unit 204, predictive battery power consumption calculating unit 205 and display unit 206, calculates predictive battery power consumption 250 using imaging list 210, power consumption table by target region 220 and moving power consumption 230 and detects remaining battery power 240.

Figure 3:
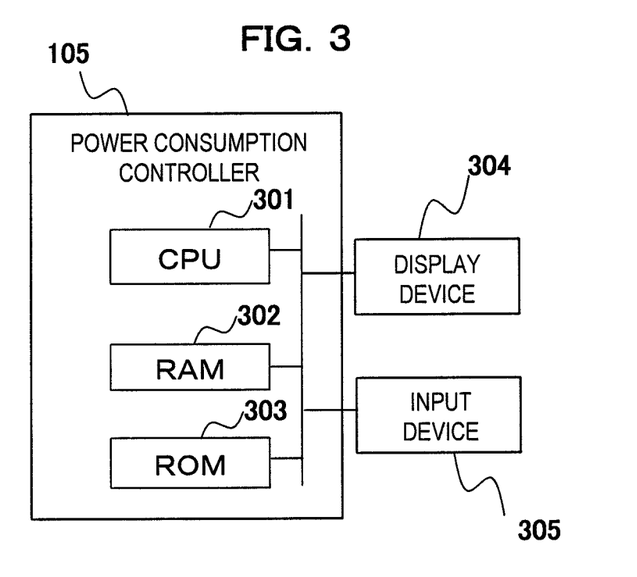
FIG. 3 is a hardware block diagram of the power consumption controller in an embodiment of the present invention.

As shown in FIG. 3, power consumption controller 105 comprises central processing unit (CPU) 301 for controlling operation of the respective components, RAM 302 for temporarily storing data etc. for CPU 301 to execute processing, ROM 303 for storing various data or control program, display unit 304 for displaying the processing result, and input device 305 for receiving the input of various commands.

The above-described respective functions are achieved by loading the control program stored in ROM 303 to RAM 302 to be executed by CPU 301. Display device 304 and input device 305 of power consumption controller 105 may be configured to be used also as display unit 104 and input unit 103 of mobile-type X-ray apparatus 100. Also, mobile-type X-ray apparatus 100 may comprise the device having configuration connectable to a network in hospitals (for example, a CR device or FPD device).

Figure 4:
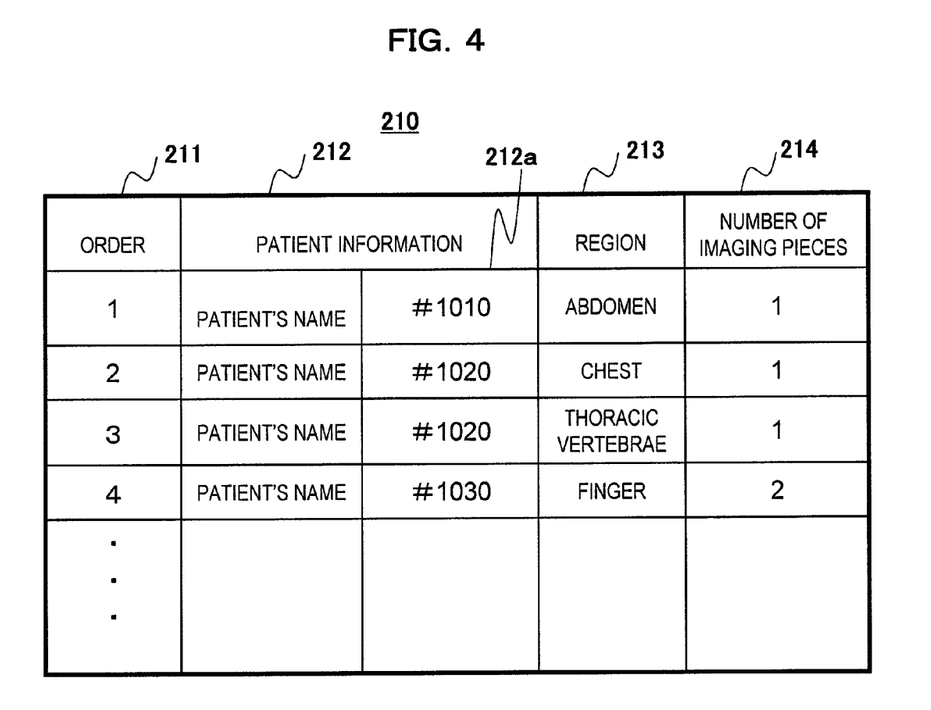
FIG. 4 is for explaining an imaging list in an embodiment of the present invention.

Imaging list controller 201 controls imaging list 210 which is inputted via input device 305 and stored in ROM 303. Imaging list 210 contains the list of imaging examinations planned for one round, and a target region to be imaged for each patient and the number of imaging times are registered. FIG. 4 is for explaining imaging list 210. On the imaging list 210, the information for specifying the imaging order (order information) 211, the information for specifying the patient (patient information) 212, the information for specifying the imaging target region (target region information) 213 and the number of imaging times 214 are registered as imaging data for each imaging as shown in FIG. 4. In patient information 212, patient ID 212a for uniquely specifying the respective patients is registered. Also, imaging list controller 201 notifies predictive battery power consumption calculating unit 205 when imaging list 210 is newly inputted or updated. In the case that mobile-type X-ray apparatus 100 has a device having configuration connectable to a network in hospitals, imaging list 210 may be configured to be inputted or updated via the device. Further, imaging list 210 may be comprised in the foresaid device.

Imaging list controller 210, upon receiving the notification from imaging controller 106 that a certain imaging is completed, deletes the imaging data of the completed imaging and updates imaging list 210. At this time, imaging order information 211 of the imaging data after the deleted imaging is moved forward one by one. Also, when new imaging is added, imaging data added in the assigned imaging order is inserted, and imaging order information 211 of the imaging data after the inserted imaging is to be moved down for the number of the inserted imaging data. Such control process is to be continued, for example until the command to end the rounds is received via input device 305.

Figure 5:
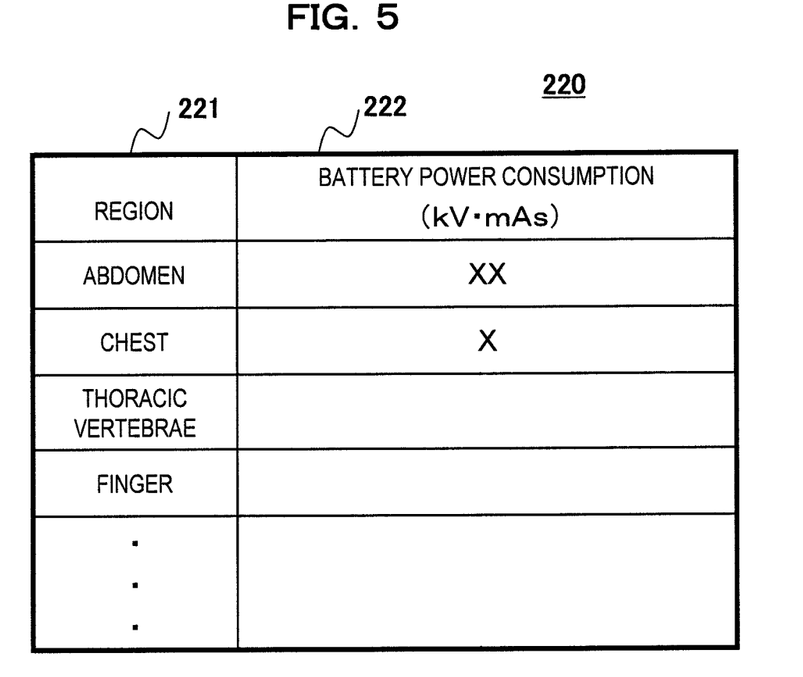
FIG. 5 is for explaining a power consumption table by target region related to an embodiment of the present invention.

In power consumption table 220 for each region, the power consumption according to the imaging target region is registered. FIG. 5 is for explaining power consumption table 220 for each target region. In power consumption table 220 by target region, an available power consumption of mobile-type X-ray apparatus 100 to execute imaging for each imaging region 221 (battery power consumption information) 222 is stored. As for battery consumption information 222, for example tube voltage (kV) and tube current time integration (mAs) to be required upon imaging each target region are registered. Also, power consumption table 220 by target region is stored in ROM 303 in advance. In the case that mobile-type X-ray apparatus 100 comprises the device connectable to a network in a hospital, power consumption table 220 may be stored outside of mobile-type X-ray apparatus 100.

The electric energy to be consumed upon moving among patients (moving power consumption) is controlled as moving power consumption 230. The pre-set values are registered in ROM 303 as moving power consumption 230.

Remaining battery power detecting unit 204 detects the sufficient electric energy which rechargeable battery 108 can supply being set off by predetermined time intervals or occurrence of a predetermined event, stores the detected energy in ROM 303 as remaining battery power 240, and notifies it to display processor 206. For detection of remaining battery amount 240, a commonly known method for detecting remaining battery amount is to be used. For example, sufficient power supply amount is calculated by detecting the output current from rechargeable battery 108.

Predictive battery power consumption calculating unit 205, when receiving the command from the user or the notification from imaging list controller 201 that imaging list 210 is updated, calculates the power consumption for executing the entire imaging registered in imaging list 210 as predictive battery power consumption 250. Predictive battery power consumption 250 is a sum of the predictive imaging power consumption to be consumed in imaging itself and predictive moving power consumption to be consumed in moving mobile-type X-ray apparatus 100 among imaging examinations.

For calculating predictive imaging power consumption, power consumption for the number of scanning times for each patient or target region is calculated and summed, using power consumption information 222 stored in power consumption table by target region 220 corresponding to target 221 which accords with target region information 213 on imaging list 210. Also, predictive moving power consumption is to be obtained by multiplying the number of patients registered in imaging list 210 by moving power consumption 230. The number of patients is to be counted using patient ID 212a in imaging list 210. Predictive battery power consumption calculating unit 205 notifies the calculated predictive battery power consumption 250 to display processing unit 206.

Figure 6:
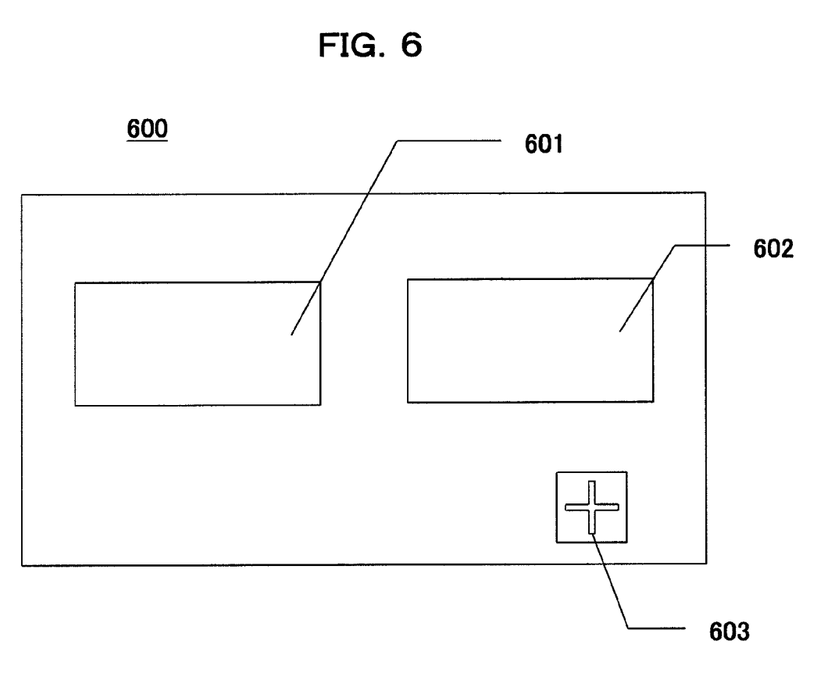
FIG. 6 is for explaining an example of a display screen related to an embodiment of the present invention.

Display processing unit 206 generates display data for displaying remaining battery power 240 and predictive battery power consumption 250 on display unit 304. FIG. 6 is for explaining an example of display screen 600 formed by display data. Display screen 600 comprises first display section 601 and second display section 602. Remaining battery power 240 is displayed on first display section 601 and predictive battery power consumption 250 is displayed on second display section 602 respectively. The display of remaining battery power 240 and predictive battery power consumption 250 are updated respectively upon receiving the notification. These figures are displayed, for example on percentage (0%~100%) with respect to the electric energy in the case that rechargeable battery 108 is recharged 100%.

Display device 304 may comprise command button 603 for receiving the command to switch the content of display. Display processing unit 206 receives the command to change the display via command button 603 and changes, for example remaining battery amount 240 and predictive battery power consumption 250 from the above-mentioned numeric display to a chart display. The method for displaying remaining battery amount 240 and predictive battery power consumption 250 are not limited thereto. Any display pattern that is easy for the user to capture the amount values visually may be used such as graph display, meter display or digital display.

Figure 7:
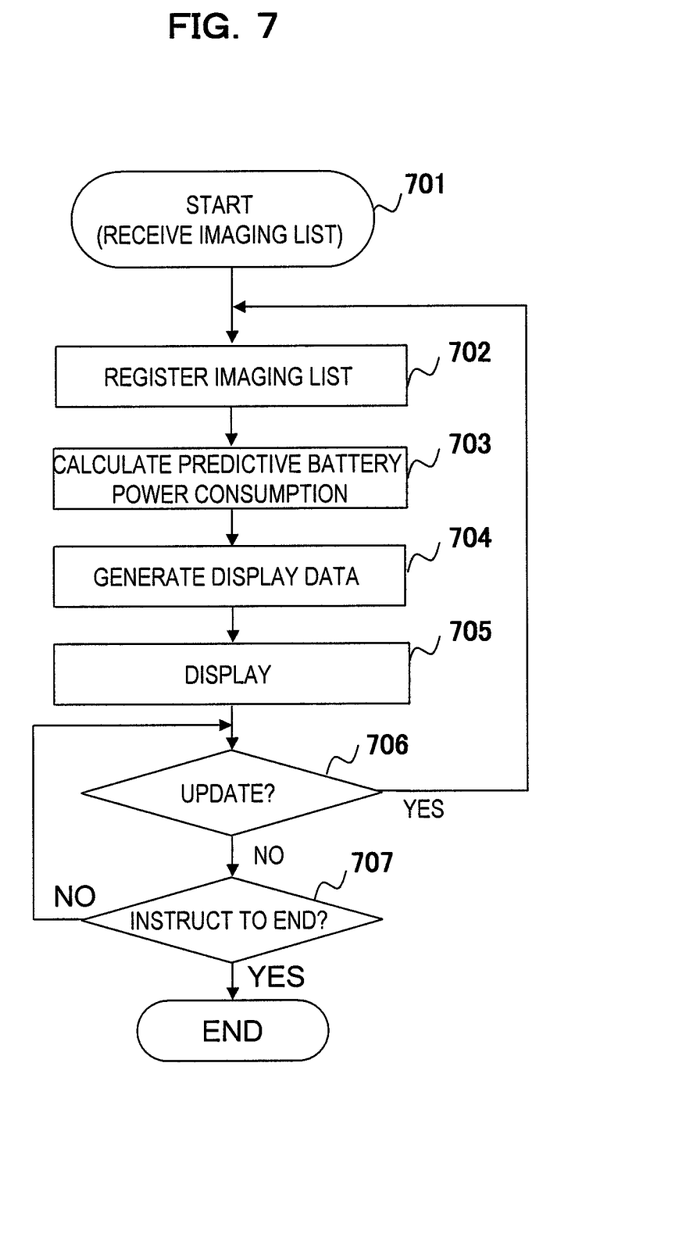
FIG. 7 is a flowchart showing a process for displaying predictive battery power consumption related to an embodiment of the present invention.

Next, predictive battery power consumption 250 of the present embodiment is calculated and displayed. The processing flow for displaying the predictive battery power consumption by power consumption controller 105 will be described. Here, the case that starts the process on the basis of the registration of imaging list 210 will be exemplified. FIG. 7 is a flowchart showing the display process of predictive the battery power consumption. Here, the case that calculates predictive battery power consumption 250 for every update of imaging list 210 will be exemplified. It also may be configured such that the above-mentioned calculation is executed only when the command from the user is received. Also, remaining battery power 240 is to be detected separately at predetermined intervals.

Upon receiving the input of an imaging list via input device 305 (step 701), imaging list controller 201 registers imaging list 210 in ROM 303 (step 702), and notifies the list to predictive battery power consumption calculating unit 205. Upon receiving the notification, predictive battery power consumption calculating unit 205 calculates predictive battery power consumption 250 referring to imaging list 210 (step 703). Then it notifies the calculation result to display processing unit 206. Display processing unit 206 generates display data using the most updated remaining battery power 240 stored in remaining battery detecting unit 204 and the notified predictive battery power consumption 250 (step 704), and displays the generated data on display device 304 (step 705). After that, imaging list controller 201 monitors if imaging list 210 is updated, and also monitors the command from the user to end the rounds at predetermined timings (steps 706 and 707). When the list is updated the process returns to step 702, and when the command to end the rounds is received the process is to be ended.

Also, in the case that mobile-type X-ray apparatus 100 is the kind in which imaging list is stored in advance such as a CR device or FPD device, for example power consumption controller 105 executes the above-mentioned step 703 and subsequent steps thereof being set off by receiving of the command from the user to start calculating the predictive battery power consumption via input device 305.

As mentioned above, in accordance with the present embodiment, not only the remaining battery power at the present time but also the predictive battery power consumption planned to be consumed in the subsequent imaging examinations is displayed on the display unit. The approximate estimate of the power consumption to be consumed by moving of mobile-type X-ray apparatus 100 in rounds is also included in the predictive battery power consumption. Therefore, it is possible to acquire the predictive battery power consumption calculated with high accuracy. Also, the user can easily determine whether to execute the imaging registered in the imaging list or to recharge the battery by comparing the remaining battery power and the predictive battery power consumption.

Also, the predictive battery power consumption is updated in accordance with the update of the imaging list. Therefore, even in the situation such as addition of imaging, requirement for re-imaging or emergency imaging occurs, it is possible to identify accurate predictive battery power consumption which leads to quick response to the change of examination plan.

While the above-described embodiment calculates and displays predictive battery power consumption 250 of along with remaining battery power 240, the display content is not limited thereto. For example, it may be configured to display the predictive power supply that rechargeable battery 108 can supply (predictive remaining battery amount) after executing the entire imaging registered in imaging list 210. Predictive remaining battery power is calculated, after calculating predictive battery power consumption 250 by predictive battery power consumption calculating unit 205, by subtracting predictive battery power consumption 250 from remaining battery power 240 at the present time point. Then display processing unit 206 displays the predictive remaining battery power on display device 304 along with remaining battery power 240. Also, when the predictive battery power becomes minus, the information indicating "shortage" may be displayed.

Also, it may be configured to display the information indicating up to which point in imaging list 210 can be imaged (available imaging list) with remaining battery power 240 at the present time. In this case, predictive battery power consumption calculating unit 205 repeats subtracting from remaining battery power 240 the battery power consumption necessary for executing the imaging and subtracting the moving power consumption each time the patient information is changed in the order of imaging list 210, until the result ends up as minus. When the result ends up as minus, predictive battery power consumption calculating unit 205 determines that the imaging can be executed until the imaging data just before the power runs out and notifies, for example order number information 211 of the imaging data just before the power runs out to display processing unit 206. In the case that the result does not reach minus when the entire list in imaging list 210 is processed, the information indicating that the entire imaging can be executed is notified to display processing unit 206. Display processing unit 206 displays the available imaging list along with remaining battery power 240.

As for the display pattern of the available imaging list, for example the entire imaging data available to be imaged from among imaging list 210 may be displayed, the imaging data determined as available to be imaged may be displayed in an identifiable manner, or the maximum number from among order number information 211 of the imaging data determined as available to be imaged may be displayed.

Also, the number of image pieces available to be imaged for each target region (the available imaging pieces by target region) may be calculated and displayed using not the predictive battery power consumption based on imaging list 210 but by remaining battery power 240. Predictive battery power consumption calculating unit 205 calculates the number of available imaging pieces for each target region using power consumption information 222 for each target region stored in power consumption table 220 for each target region. Display processing unit 206 displays the number of available imaging pieces for each target region on display device 304. The electric consumption energy to be consumed in imaging is different by each target region. Therefore, obtaining the number of available imaging pieces for each target region facilitates the user to easily change the plan for the rounds by using the obtained information as a guide.

Mobile-type X-ray apparatus 100 of the present embodiment may have the configuration capable of calculating and displaying one or more items from among predictive battery power consumption 250, predictive remaining battery power, available imaging list and available number of imaging pieces for each region. Also, it may have the configuration that enables the user to select which items are to be displayed. By having the capability to display a plurality of items, the user can identify whether or not he/she can execute the imaging on an imaging list more easily.

Further, it may be configured that a predictive remaining battery power, available imaging list and available number of imaging pieces for each region are calculated and displayed also when remaining battery power 240 changes more than a predetermined value from the previous calculation, in addition to when receiving a command from the user or imaging list 210 is updated. This configuration is provided with the function to store the remaining battery power at the time of calculation, and to compare the remaining battery power at the time of update with the stored remaining battery power. In this manner, when there is a significant change in the remaining battery power, for example in the cases that no imaging is executed while mobile-type X-ray apparatus 100 is running or an unexpected long distance movement is required, more accurate calculation result can be obtained.

Figure 8:
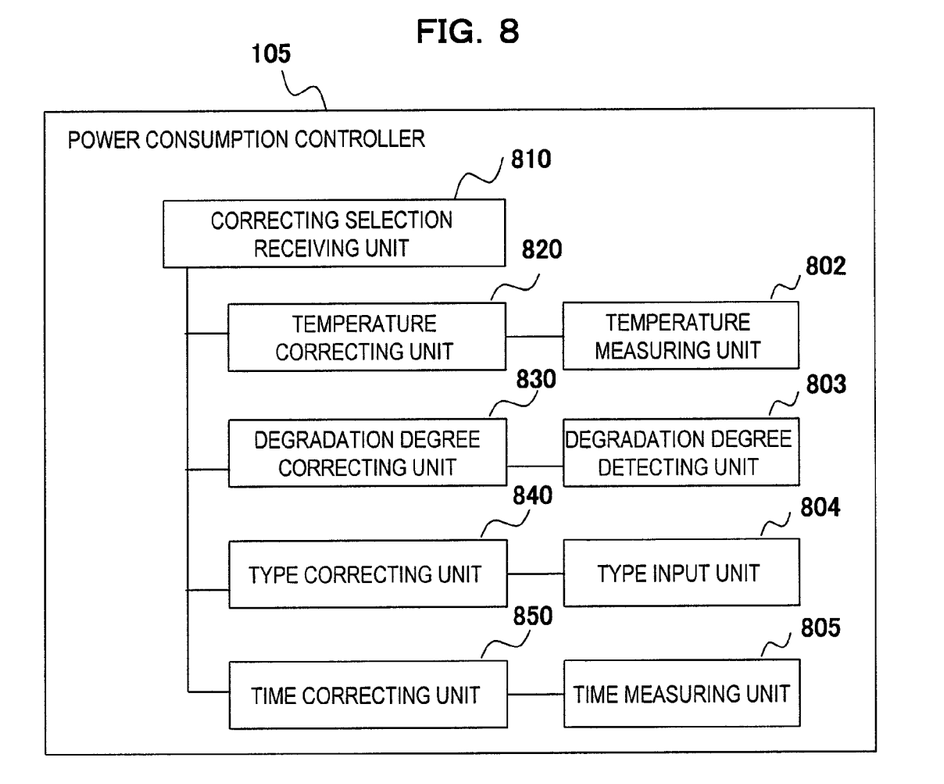
FIG. 8 is a functional block diagram for correcting the power consumption controller related to an embodiment of the present invention.

Further, the present embodiment may be configured capable of executing various corrections upon calculation of the above-mentioned various items by predictive battery power consumption calculating unit 205. Also, the corrections to be considered may be selected by a user. Here, the case will be exemplified that correction can be made on operating time, temperature at the environment of usage, degradation, and device type of rechargeable battery 108. The additional configuration to power consumption controller 105 required to execute these corrections is shown in FIG. 8.

Power consumption controller 105 comprises correcting selection receiving unit 810, temperature measuring unit 802 and temperature correcting unit 820 for making correction due to the temperature at the environment of usage, degradation degree detecting unit 803 and degradation degree correcting unit 830 for making correction due to degradation of battery, device type input unit 804 and device type correcting unit 840 for making correction due to the type of the device being used, and time measuring unit 805 and time correcting unit 850 for making correction due to operating time (passage of operating time). Correcting selection receiving unit 810 gives command to the respective units via input device 305 to execute only the selected correction.

Generally, available energy capacity of a battery changes according to the temperature at the environment of usage. When the temperature drops, available energy capacity decreases and remaining battery power 240 also decreases. In order to measure the temperature of rechargeable battery 108 at the environment of usage, temperature measuring device 802 is placed in the vicinity of rechargeable battery 108. As for temperature measuring device 802, for example a thermistor is used. When the command to consider correction due to temperature is received by correcting selection receiving unit 810, temperature correcting unit 820 calculates the correction value for correcting remaining battery power 240 using the temperature measured by temperature measuring device 802. The correction value is calculated using correlative information between the temperature and the change in battery capacity and correlative information between the battery capacity and the available electric power that are stored in advance. Then the correction value is notified to remaining battery power detecting unit 204. Remaining battery power detecting unit 204 corrects the detected remaining battery power 240 detected using the correction value.

Also, generally a battery deteriorates as being used. In accordance with the degradation of battery, the battery power consumption also varies. When the command to consider the correction due to degradation of battery is received by correcting selection receiving unit 810, degradation detecting unit 803 detects the voltage or current at the time of high-load usage such as during imaging or moving. Degradation degree detecting unit 830 compares the power consumption calculated from the detected voltage or current and the pre-stored power consumption at the time of high-load condition, determines the degradation degree of rechargeable battery 108, calculates the correction value for correcting the remaining battery power, and notifies the calculated power to remaining battery power detecting unit 204. Remaining battery power detecting unit 204 corrects the remaining battery power 240 using the correction value.

In the case that mobile-type X-ray apparatus 100 has the function besides the imaging function such as for connecting to a network in a hospital, for example a CR device or FPD device, the electric power consumption increases for the amount to operate those functions. When the command to consider the correction due to the type of device is received by correcting selection receiving unit 810, type input unit 804 receives the information to specify the type of device via input device 305. Type correcting unit 840 stores the information to specify the increase of electric power consumption according to the respective devices, and extracts the electric power consumption (increasing portion) according to the received type of device. Then it notifies the extracted increasing portion of the electric power consumption to predictive battery power consumption calculating unit 205. Predictive battery power consumption calculating unit 205 adds the received increasing portion to the calculated predictive battery power consumption 250 to make it zero.

Type input unit 804 may be configured to input not only the type of device but also the information for specifying a user. In this case, type correcting unit 840 stores the variation portion of the electric power consumption according to a user, and notifies the obtained increasing portion to predictive battery power consumption calculating unit 205.

When mobile-type X-ray apparatus 100 is running without imaging for a long period of time, the output of rechargeable battery 108 decreases. However, predictive battery power consumption calculating unit 205 does not execute the process unless imaging list 210 is updated or the command from a user is received. Therefore, when one kind of calculation is executed from among the calculations for predictive remaining battery power, available imaging list or the number of available imaging piece for each region, there is a possibility that the accuracy of these calculation results is lowered. When the command to consider the correction due to passage of time is received by correcting selection receiving unit 810, time measuring unit 805 measures the passage of time from the previous calculation executed by predictive battery power consumption calculating unit 205. Time correcting unit 850 monitors the measurement by time measuring unit 805, and when determination is made that more time has passed than a predetermined time, gives the command to predictive battery power consumption calculating unit 205 to execute re-calculation. Then it makes the correction by replacing predictive battery consumption 250 with the obtained result. By employing the above-described correction, it is possible to reflect the lowering of a battery output on a timely basis in the case that the imaging is not executed for a long period of time while mobile-type X-ray apparatus 100 is running.

As described above, by providing with the configuration capable of executing various types of correction, predictive battery power consumption can be presented to a user with a higher accuracy, and the timing for recharging a battery can also be determined more accurately.

The present embodiment also may be configured as capable of selecting whether or not to consider the predictive moving power consumption. When the command to consider the predictive moving power consumption is received via input device 305 is selected, power consumption controller 105 causes predictive battery power consumption calculating unit 205 to calculate also the predictive moving power consumption. Also, moving power consumption 230 does not have to be provided. In this case, predictive battery power consumption calculating unit 205 calculates only the predictive power consumption for imaging as the predictive battery power consumption. For example, in the case that mobile-type X-ray apparatus 100 is mainly moved manually, it is possible to obtain sufficiently accurate information with such easy processing.

Also, the present embodiment may be configured capable of correcting moving power consumption 230 according to the used facility (hospital). This is because the moving distance per patient differs largely depending on the size of the facility.

Also, the present embodiment may be configured as capable of updating moving power consumption 230. That is, the moving power consumption is calculated from the actual moving power consumption and the calculated power consumption is to be replaced with the newest calculation result at each round.

Figure 9:
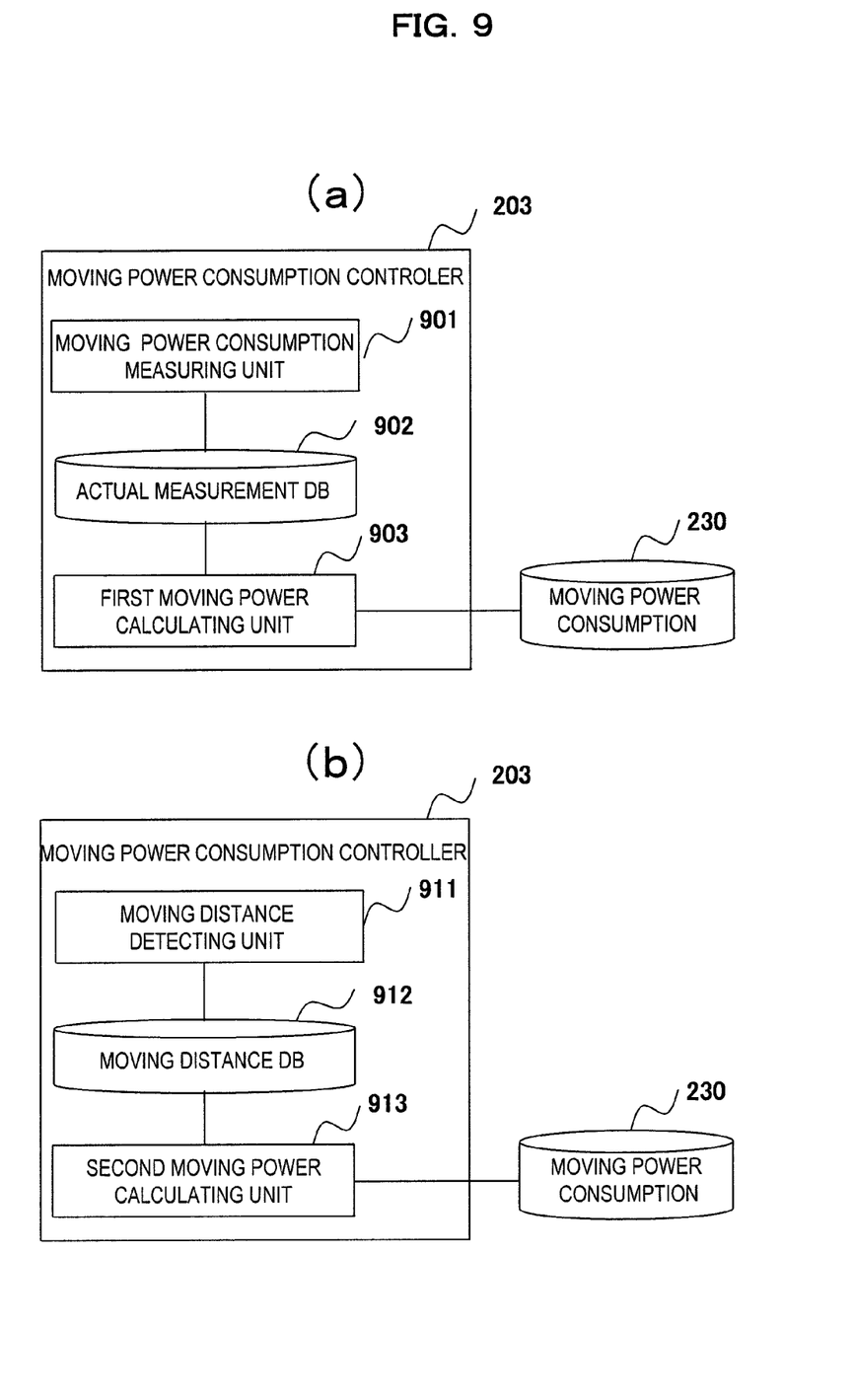
FIG. 9 is a functional block diagram for updating the moving power consumption in the power consumption controller related to an embodiment of the present invention.

In order to achieve the above-mentioned function, electric consumption controller 105 comprises moving power consumption controller 203 that updates moving power consumption 230 as shown in FIG. 9(*a*). Moving power consumption 203 comprises moving power consumption measuring unit 901 for measuring the actual power consumption at the time of moving from the variation etc. of the remaining battery power, actual measurement database 902 for storing the actual moving power consumption wherein the measured power consumption is divided by the number of patients who received imaging examination for a portion of the predetermined previous numbers of measuring times, and first moving power consumption calculating unit 903 for calculating the average of the stored actual moving power consumption as the updated moving power consumption 230.

Also, when the power consumption according to the unit moving distance is clarified, the present embodiment may be configured to update the moving power consumption based on the average moving distance for making one round. In order to achieve the above-mentioned configuration, moving power consumption controller 203 is to be placed in the vicinity of wheel 107 of moving carriage 106, and comprises moving distance detecting unit 911 for detecting the moving distance from the number of rotations of wheel 107, moving distance database 912 for storing the moving distance detected by moving distance detecting unit 911 for the predetermined previous numbers of imaging times, and second moving power consumption calculating unit 913 for calculating moving power consumption 230 by calculating the average of the moving distances stored in moving distance database 912, multiplying the calculated average value by the electric power consumption according to the above-mentioned unit moving distance and dividing the multiplied value by the number of patients who received an imaging examination in the rounds, as shown in FIG. 9(*b*).

As described above, by providing the configuration capable of updating moving power consumption 230, accuracy in calculating the predictive moving power consumption can be further improved.

Further, while the above-described embodiment is configured to update the content to be displayed on display device 304 according to the command from command button 603, the present embodiment is not limited thereto. For example, in the case that display device 304 is used also as display unit 104 for setting and displaying the imaging condition of mobile-type X-ray apparatus 100, it may be configured to display the information related to rechargeable battery 108 such as remaining battery power 240 and predictive battery power consumption 250 while the apparatus is moving and to execute usual display while the apparatus is not moving.

In this case, for example the present embodiment comprises a brake-release detecting unit for detecting release of a break and a display data switching unit, and switches the display data on display unit 104 when the break-release detecting unit detects that the break is released.

By comprising the above-described configuration, it is possible to obtain the necessary information at necessary situations with simple configuration.

Description Of Reference Numerals

100: mobile-type X-ray apparatus, 101: main body, 102: X-ray generator, 103: input unit, 104: display unit, 105: electric consumption controller, 106: moving carriage, 107: wheel, 108: rechargeable battery, 109: imaging controller, 201: imaging list controller, 204: remaining battery power detecting unit, 205: predictive battery power consumption calculating unit, 206: display processing unit, 210: imaging list, 211: order information, 212: patient information, 212*a*: patient ID, 213: region information, 214: number of imaging pieces, 220: power consumption table for each region, 221: region, 222: power consumption information, 230: moving power consumption, 240: remaining battery power, 250: predictive battery power consumption, 301: CPU, 302: RAM, 303: ROM, 304: display device, 305: input device, 600: display screen, 601: first display section, 602: second display section, 603: command button, 802: temperature measuring unit, 803: degradation degree detecting unit, 804: type input unit, 805: time measuring unit, 810: correcting selection receiving unit, 820: temperature correcting unit, 830: degradation degree correcting unit, 840: type correcting unit, 850: time correcting unit, 901: moving power consumption measuring unit, 902: actual measurement database, 903: first moving power consumption calculating unit, 911: moving distance detecting unit, 912: moving distance database, 913: second moving power consumption calculating unit

The invention claimed is:

1. A mobile-type X-ray apparatus for executing X-ray imaging examinations with a battery as a drive source, comprising:
   remaining battery power detecting means configured to detect the power remains in the battery;
   predictive battery consumption calculating means configured to calculate predictive battery power consumption based on an imaging list containing a list of scheduled X-ray imaging examinations;
   display means configured to display the remaining battery power and the predictive battery power consumption; and
   correcting means configured to correct the predictive battery power consumption or the remaining battery power according to a factor that chances the remaining battery power or the predictive battery power consumption.

2. The mobile-type X-ray apparatus according to claim 1, wherein the predictive battery power consumption includes the battery power consumption for executing the entire X-ray imaging registered in the imaging list.

3. The mobile-type X-ray apparatus according to claim 2, wherein the mobile-type X-ray apparatus is capable of moving by the battery as the drive source, and a battery power consumption for the moving is further included in the predictive battery power consumption for executing the entire X-ray imaging registered in the imaging list.

4. The mobile-type X-ray apparatus according to claim 3, further comprising:
   moving power consumption control means configured to control a moving power consumption which is the battery power consumption according to an average moving distance for each patient who receives an imaging examination;
   actual measurement means configured to measure the moving power consumption; and
   moving power consumption updating means configured to update moving power consumption controlled by the moving power consumption control means using the moving power consumption measured by the actual measurement means,
   wherein the battery power consumption for moving is calculated using the moving power consumption controlled by the moving power consumption control means.

5. The mobile-type X-ray apparatus according to claim 1, wherein the predictive battery power consumption includes the battery power in which the battery power consumption for executing the entire X-ray imaging registered in the imaging list is subtracted from the remaining battery power.

6. The mobile-type X-ray apparatus according to claim 1, wherein the predictive battery power consumption includes information that specifies the available X-ray imaging to be executed by the remaining battery power in the case that the X-ray imaging registered in the imaging list is to be executed in the registered order.

7. The mobile-type X-ray apparatus according to claim 1, wherein the predictive battery power consumption includes a number of imaging pieces available to execute X-ray imaging for each imaging target region with the remaining battery power.

8. The mobile-type X-ray apparatus according to claim 1, further comprising:
   correction command receiving means configured to receive a command that specifies items to correct from among a plurality of factors.

9. The mobile-type X-ray apparatus according to claim 8, further comprising:
   degradation degree detecting means configured to detect a voltage and a current at the time of operating the mobile-type X-ray apparatus when degradation of the battery is received as the factor for executing correction by the correction command receiving means; and
   degradation degree correction calculating means configured to calculate the battery power consumption from the voltage and the current detected by the degradation degree detecting means, calculate a correction value for correcting the remaining battery power from the calculated remaining battery power and the battery power consumption at the operating time which is stored in advance, and notify the correction value to the correcting means.

10. The mobile-type X-ray apparatus according to claim 1, further comprising:
   input means configured to receive a command to update the imaging list; and
   imaging control means configured to execute the X-ray imaging according to the imaging list;
   imaging list control means configured to update the imaging list by updating the imaging list when the command to update the list via the input means is received and by deleting the X-ray imaging from the imaging list when the X-ray imaging on the imaging list is executed by the imaging control means,
   wherein the predictive battery consumption calculating means calculates the predictive battery power consumption when the imaging list is updated by the imaging list control means.

11. The mobile-type X-ray apparatus according to claim 10, wherein the input means further receives the input of the imaging list itself.

12. The mobile-type X-ray apparatus according to claim 11, wherein the input means receives the input and update of the imaging list via a network.

\* \* \* \* \*